(12) United States Patent
Weese et al.

(10) Patent No.: US 8,175,358 B2
(45) Date of Patent: May 8, 2012

(54) APPARATUS AND METHOD FOR THE PROCESSING OF PERFUSION IMAGES

(75) Inventors: Jürgen Weese, Aachen (DE); Georg Rose, Düsseldorf (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 976 days.

(21) Appl. No.: 10/598,305

(22) PCT Filed: Mar. 4, 2005

(86) PCT No.: PCT/IB2005/050810
§ 371 (c)(1),
(2), (4) Date: Jul. 7, 2008

(87) PCT Pub. No.: WO2005/087107
PCT Pub. Date: Sep. 22, 2005

(65) Prior Publication Data
US 2008/0260231 A1  Oct. 23, 2008

(30) Foreign Application Priority Data

Mar. 4, 2004 (EP) .................................. 04100879

(51) Int. Cl.
G06K 9/00 (2006.01)
(52) U.S. Cl. ....................................... 382/131; 382/132

(58) Field of Classification Search ................... 382/128, 382/130, 131, 132; 378/4, 98.12, 901
See application file for complete search history.

(56) References Cited

U.S. PATENT DOCUMENTS

| | | | |
|---|---|---|---|
| 5,802,220 | A | 9/1998 | Black et al. |
| 6,373,920 | B1 | 4/2002 | Hsieh |
| 2003/0055410 | A1 | 3/2003 | Evans et al. |

OTHER PUBLICATIONS

Herman et al; "Algebraic Reconstruction Techniques Can be Made Computationally Efficient"; IEEE TMI 12 (3), P.600FF, 1993.
Beekman et al; "Fast Ordered Subset Reconstruction for XX-Ray CT"; IEEE Nuclear Science Symposium Conference Record; vol. 2, 2000.

*Primary Examiner* — Jurie Yun

(57) ABSTRACT

The invention relates to an apparatus and a method for the reconstruction of time-dependent cross-sectional images and may be applied for example in perfusion imaging in the vessel system (2) of a patient. According to the method, projections $p^i_j$ are generated from a number M of different directions $d^i$ and at different times $t^i_j$. Moreover, the time-dependent intensity function $I(x,t)$ of the reconstructed volume is approximated by a predetermined model function $I^*(a(x),t)$, wherein the unknown parameter vector $a(x)$ is estimated for each voxel x. This estimation may be done using the update functions of known reconstruction algorithms like ART for at least N projections $p^i_j$ in each iteration step.

19 Claims, 2 Drawing Sheets

APPARATUS AND METHOD FOR THE PROCESSING OF PERFUSION IMAGES

The invention concerns an image processing apparatus and a method for the reconstruction of time-dependent representations of an object, particularly during perfusion imaging. Moreover the invention relates to an X-ray examination system comprising such an apparatus and a computer program implementing said method as well as to an X-ray system.

Perfusion imaging is an important functional imaging method in medical applications which delivers information about the blood supply of the tissue and the tissue viability as well as valuable information during interventions. According to current techniques, perfusion imaging requires the acquisition of a time series (with typically about 40 members) of (multiple) cross-sectional images with a frame rate in the order of 0.75-1 second. After acquisition and reconstruction of the individual cross-sectional images, the image time series is evaluated and a perfusion map is computed.

In a perfusion imaging procedure described in the U.S. Pat. No. 6,373,920 B1, a first set of projections is taken without contrast agent and later a second set of projections is taken with contrast agent. From the difference of the images reconstructed based on each set, a perfusion image is calculated.

As current C-arm X-ray systems are limited in their rotational speed and detector frame rate, such systems cannot be used for perfusion imaging based on cross-sectional images generated in short time intervals.

Based on this situation it was an object of the present invention to provide means for a facilitated perfusion imaging, especially by use of normal C-arm based X-ray systems.

This object is achieved by an image processing apparatus, an X ray examination system, a method, a computer program, a record carrier, and an X-ray system as disclosed herein.

According to a first aspect the invention comprises an image processing apparatus for the reconstruction of time-dependent representations $I(x,t)$ of an object. The apparatus may be realised by a computer together with appropriate programs to execute the required image processing. The reconstructed representations may especially be two-dimensional or three-dimensional cross-sectional images of the object, and the object may particularly be the vessel system of a patient where perfusion shall be investigated or where the flow of a contrast agent shall be reconstructed. As perfusion is a time-varying process, the respective cross-sectional images are not stationary but time-dependent, too. The apparatus is adapted to approximate the function $I(x,t)$ by a given parametric model function $I^*(a(x),t)$ and to estimate the N-dimensional parameter vector $\overline{a(x)}$ with the help of a set of projections $p^i_j$ of the object (2) generated at times $t^i_j$. To accomplish this functionality, the apparatus comprises the following components:

An approximation module with memory storing the N-dimensional parameter vector $a(x)$ of the predetermined parametric model function $I^*(a(x),t)$ that approximates the function $I(x,t)$, wherein $I(x,\overline{t})$ describes the representation of the object. Each value of the function $I(x,t)$ may for example describe the attenuation coefficient or the image signal (e.g. the grey-value) of a particular voxel x at time t. If three-dimensional cross-sectional images are reconstructed, $I(x,t)$ is a function depending on four independent variables. The model function $I^*(a(x),t)$, in contrast, depends on the N-dimensional parameter vector a and time t in a known manner, because $I^*(a(x),t)$ is constructed or pre-selected by the user of the apparatus. All you have to know to describe the representation of the object (e.g. a cross-sectional image) with $I^*(\underline{a}(x),t)$ is then the spatial dependence of the parameter vector $a(x)$. In other words the problem of finding a spatially dependent functional $I(x,\bullet)$ for a continuum of times t is reduced to finding N spatially dependent functions $a(x)$.

An input module for the reception of a set of projections $p^i_j$ of the object generated at times $t^i_j$. The input module may for example couple the image processing apparatus to an X-ray device generating said projections.

An estimator or estimation module that is adapted to estimate the N-dimensional parameter vector $a(x)$ with the help of a set of projections $p^i_j$ of the object, wherein each projection $p^i_j$ is produced at some time $t^i_j$, and wherein the times $t^i_j$ are typically different from each other. Possible ways to realize such an estimation module are described in connection with preferred embodiments of the invention.

By approximating the real function $I(x,t)$ by a parametric function $I^*(a(x),t)$, the apparatus reduces the complexity of the reconstruction problem considerably. Moreover, this approximation has the advantage to allow an estimation of the parameter vector a and therefore of the desired representation of the object by projections $p^i_j$ that may in principle be arbitrarily distributed over time. In particular, it is not necessary to produce whole sectional images of a (quasi) stationary situation for various time points which is for example not possible in perfusion imaging with a C-arm based X-ray system. With the described apparatus, however, such systems become applicable, and the projections generated by a C-arm system during one or more sweeps may be used.

Further, the invention provides an X-ray system suitable for determining a 3D dynamic process in an object, the system comprising an x-ray source and an x-ray detector placed at opposite positions with respect to an examination space and simultaneously rotatable around said examination space for generating a plurality of x-ray projections;

a data processing unit for deriving from said plurality of x-ray projections a map of the time dependent 3D dynamic process in the object;

whereby the 3D dynamic process is approximated by a predetermined model with a limited set of parameters;

whereby the data processing unit is arranged to estimate parameters in said limited set of parameters out of data in the x-ray projections.

According to a preferred embodiment of the invention, the apparatus comprises an evaluation module for the determination of a perfusion map from the representation $I(x,t)$ of a vessel system. If the representation $I(x,t)$ and its approximation $I^*a(x),t)$ for instance describe for each time t a cross-sectional image of the object, perfusion parameters may readily be calculated therefrom and represented in a perfusion map.

The representation $I(x,t)$ of the object and its approximation $I^*(a(x),t)$ may in general relate to any spatially distributed entity characterizing the object and derivable from projections. In a special embodiment that will be considered in more detail below, the functions $I(x,t)$ and $I^*(a(x),t)$ describe for each point t in time a cross-sectional image through the object.

According to a first approach to calculate the desired parameter vector $a(x)$ of a function $I(a(x),t)$ representing a cross-sectional image, the apparatus is adapted to use an update function $\Delta I(x, p^{i(k)}, I^k(x))$ for the estimation of the parameter vector a, wherein the update function $\Delta I(x, p^{i(k)}, I^k(x))$ is taken from an iterative algorithm for the reconstruction of stationary cross-sectional images $I(x)$. One important example for such an algorithm is known as "Algebraic Reconstruction Technique" (ART). Update functions based on this algorithm or derivatives thereof are especially suited for the present estimation method. In the update function, $p^{i(k)}$ is a projection of an object used in the k-th iteration step, and $I^k(x)$ is the k-th estimate for $I(x)$. The application of update functions of known algorithms has the advantage that well known mathematical procedures and existing tools may be exploited.

In a further development of the apparatus described above, the parameter vector $a(x)$ is iteratively approximated by a sequence $a^k(x)$, wherein the (k+1)-th iteration comprises the following steps:

a) The computation of k-th order estimates $I^*(a^k(x),t^i_j)$ for at least N of the times $t^i_j$, wherein the times $t^i_j$ may in principle be selected arbitrarily. This selection of times may be described by corresponding index sets A and B according to i∈A and j∈B (wherein A and B normally change from iteration step to iteration step).

b) The computation of corresponding updates $$\Delta I^{k,i}_j = \Delta I(x, p^i_j, I^*(a^k(x), t^i_j)),$$

wherein $\Delta I$ is the update function of a known iterative algorithm like ART. The update function makes use of said estimates $I^*(a^k(x),t^i_j)$ and the measured projections $p^i_j$ that correspond to the selected times $t^i_j$ with i∈A, j∈B.

c) The calculation are the new estimate $a^{k+1}(x)$ for the parameter vector by minimising the following function with respect to $a^{k+1}$:

$$\chi^2(x) = \sum_{i \in A, j \in B} (I^*(a^{k+1}(x), t^i_j) - I^*(a^k(x), t^i_j) - \Delta I^{k,i}_j(x))^2$$

The procedure described above will be discussed in more detail in the description of the accompanying figures. Its advantage is that it may be carried out iteratively based on standard algorithms like ART and thus may readily be implemented.

The projections $p^i_j$ of the object that are used for the estimation may in principle be arbitrarily distributed over projection angle and time, wherein the distribution should of course be such that no important developments in the processes to be observed in the object, e.g. a perfusion process, are missed. Preferably, however, the set of measured projections is structured into a number M of subsets, wherein each subset comprises only projections $p^i_j$, j=1, . . . , Q, which were taken from the same or approximately the same direction at different times. Moreover, the number Q of these projections in each subset is preferably greater or equal to the dimensionality of the parameter vector a, i.e. Q≧N. In other words there are M different projection directions, and for each of these projection directions a number Q≧N of single projections is produced at different time points. Such a structure of the projections allows to use at least N projections taken from the same direction in an iterative procedure for the estimation of $a(x)$. Thus, for example, the iterative algorithm described above may be carried out such that |A|=1 in each iteration step, provided that the times $t^i_j$ with the same superscript i belong to the same projection direction. The use of projections from the same direction in each iteration step makes the approximation procedure more stable. It should be noted at this point that the separate indices i, j of the projections $p^i_j$ were introduced to reflect the aforementioned structure of the set of projections; if there is no such structure, the indices i and j are simply symmetrical, i.e. they play the same role.

A second approach to calculate the desired parameter vector $a(x)$ for the parametric model function $I^*(a(x),t)$ may be based on the optimisation of an objective function that compares measured and calculated projections. Especially, the objective function may measure the total deviation between all measured projections $p^i_j$ and the corresponding projections $P_i I^*(a(x),t^i_j)$ that are calculated from the model function $I^*$. Such an objective function may for instance be defined by the formula $$\chi^2 = \sum_{i,j} (p^i_j - P_i I^*(a(x), t^i_j))^2.$$

An advantage of this approach is that it may readily be added to the usual image reconstruction procedures without a need to change them. Moreover, there are a priori no constraints on the kind of the used projections $p^i_j$; they may for example all belong to different projection directions and time points.

According to a further development of the apparatus, the estimation of the parameter vector a makes use of an anatomical reference data set. This reference data set may for example be a stationary cross-sectional image of the object that was produced in advance. The use of such a reference data set allows it to reduce the number of independent components in the parameter vector by one, which simplifies the estimation process accordingly. Moreover, such a reference data set is especially useful in combination with the second approach described above where it may provide an appropriate starting value for the optimization process.

The invention further relates to an X-ray examination system comprising the following components:

A rotational X-ray apparatus, for example a C-arm based X-ray system or a multi-slice CT system, for generating X-ray projections $p^i_j$ of an object from different directions.

An image processing apparatus coupled to the X-ray apparatus and adapted to approximate the function $I(x,t)$ that exactly describes the representation of an object by a given parametric model function $I^*(a(x),t)$, and to estimate the N-dimensional parameter vector $a(x)$ with the help of a set of projections $p^i_j$ of the object, wherein each projection $p^i_j$ is produced at some corresponding time $t^i_j$. The apparatus may especially be realized by a computer together with appropriate programs to execute the required image processing. Moreover, the image processing apparatus may particularly be of the kind described above.

Because the image processing apparatus allows to reconstruct time-dependent representations of an object from projections taken at different stages of the processes to be observed in the object, the rotational X-ray apparatus may especially be a conventional X-ray system with a C-arm. X-ray projections generated during one or more sweeps of such a system may be used for the reconstruction of the desired intensity function $I^*(a(x),t)$.

According to a further development of the invention, the X-ray examination system described above comprises an injection system for injecting contrast agent into the blood flow of a patient. The injection system may for example comprise a catheter and a pumping unit for controllably introducing contrast agent through the catheter into the vessel system of a patient. The injection system allows to perform perfusion imaging or reconstruction of contrast agent flow with the examination system.

The invention further comprises a method for the reconstruction of time-dependent representations of an object comprising the following steps: approximation of the function I(x,t) describing the representations by a given parametric model function I*(a(x),t); and estimation of the N-dimensional parameter vector a(x) with the help of a set of projections $p^i_j$ of the object produced at times $t^i_j$. The projections $p^i_j$ may particularly be generated with a C-arm system or a multi-slice CT system. The method comprises in general form the steps that can be executed with an image processing apparatus of the kind described above. Therefore, reference is made to the preceding description for more information on the details, advantages and improvements of that method.

Moreover, the invention comprises a computer program for enabling carrying out a method of the kind described above. Such a computer program together with a general-purpose computer may especially constitute an image processing apparatus of the kind described above.

Finally, the invention comprises a record carrier on which a computer program of the kind described above is stored. The record carrier may be any kind of permanent or volatile storage medium like RAM, ROM, hard disk, floppy disk, CD, magnetic tape or the like.

These and other aspects of the invention will be apparent from and elucidated with reference to the embodiment(s) described hereinafter.

In the following the invention is described by way of example with the help of the accompanying drawings, in which.

Figure 1:
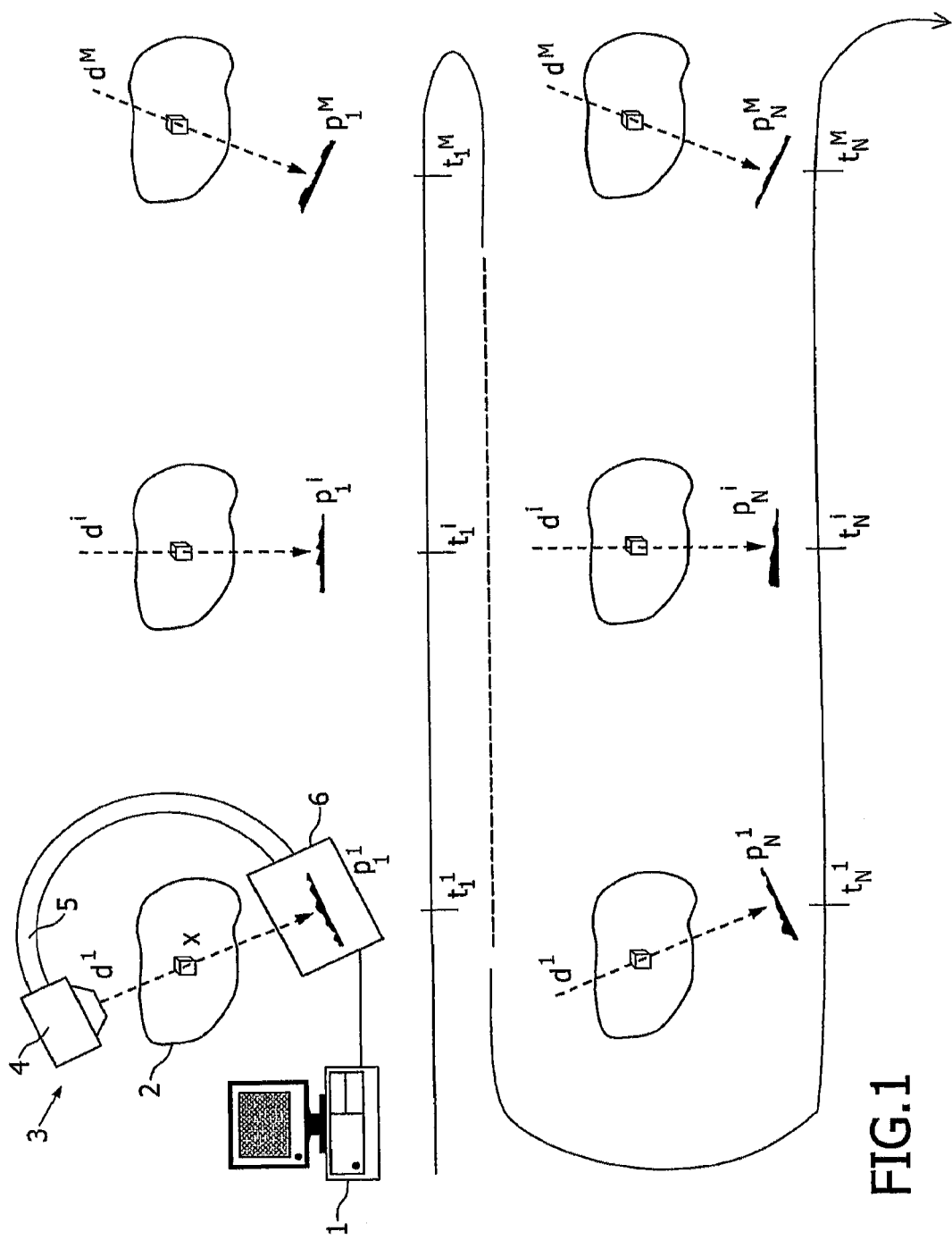
FIG. 1 is a principle sketch of an X-ray examination system and the method to generate projections for perfusion imaging according to the present invention.

The drawing in the upper left corner of FIG. 1 schematically depicts the setup of an X-ray examination system according to the present invention. The examination system comprises a rotational X-ray apparatus 3 which is adapted to generate X-ray projections of an object from different directions $d^i$, for example of the vessel system 2 of patient to be examined. The rotational X-ray apparatus 3 may especially be a conventional C-arm based X-ray system comprising an X-ray source 4 and an X-ray detector 6 connected via a C-arm 5. The X-ray apparatus 3 is connected to an image processing apparatus 1, which may for example be a workstation with appropriate software running on it.

Figure 2:
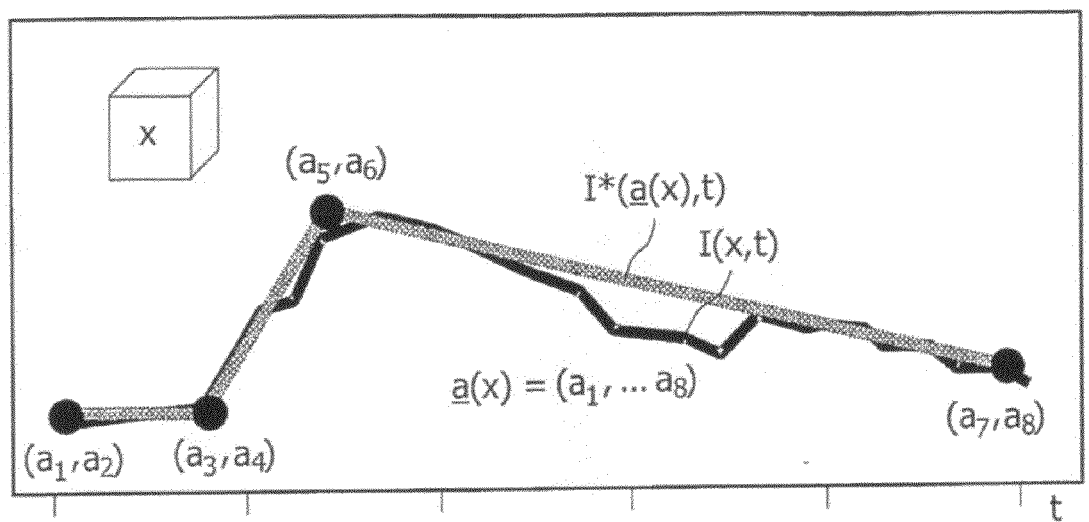
FIG. 2 is a diagram of a typical course of time-dependent grey-values and its approximation according to the present invention.

During perfusion imaging or reconstruction of flow in medical diagnostics, a contrast agent is injected into the vessel system 2 of patient by a catheter (not shown), and the spreading of this injection is monitored in order to gain information on the perfusion properties of the vessel system. Due to the temporal development of the perfusion process, the observed image signal of a voxel at position x is not constant but usually varies over time. FIG. 2 shows a typical time-dependence of the grey-value I(x,t) of a voxel x during a perfusion study (black line). The complete temporal development in the volume to be observed must therefore be described by an intensity function I(x,t) which depends on the three-dimensional position vector x (in cases of three-dimensional image reconstruction) and the one-dimensional parameter time t.

An important step of the procedure to be described in the following is the approximation of said function I(x,t) by a model function I*(a(x),t) that is predetermined by the user of the system and that depends on an N-dimensional parameter vector a and on time t in a known way. The only unknown relation will then be the spatial dependence of the parameter vector a(x). The grey curve in FIG. 2 shows a typical example of a model function I*(a(x),t) with an 8-dimensional parameter vector a(x), wherein pairs of components ($a_i$, $a_{i+1}$) describe one point in the temporal course of the model function and wherein these points are connected by straight lines. Of course a lot of other different approximations are suitable, too, for example polynomial functions or the like. The user will typically choose a model function such that it will describe the a priori expected course of intensity values with a minimal number of independent parameters.

In the following, a preferred procedure for the estimation of the parameter vector a(x) in the setup described above will be described. The procedure comprises the generation of projections $p^i_j$ with the X-ray apparatus 3 from different projection directions $d^i$ while a perfusion process is going on in the vessel system 2. In a preferred embodiment, the X-ray apparatus 3 is rotated forward and backward in such a way that for each of M projection directions $d^i$ at least N projections $p^i_j$ ($1 \leq j \leq N$) at different time points $t^i_j$ are acquired.

From the state of the art iterative reconstruction algorithms such as ART (Algebraic Reconstruction Technique) are well known (cf. e.g. G. T. Herman, L. B. Meyer; Algebraic Reconstruction Techniques can be made Computationally Efficient; IEEE TMI 12 (3), p. 600ff, 1993; F. J. Beekman, C. Kamphuis; Fast Ordered Subset Reconstruction for X-ray CT; IEEE Nuclear Science Symposium Conference Record; Volume 2, 2000). In these algorithms, the iterative reconstruction of a stationary 3D image I(x) is achieved with projections $p^i$ of an object and the recursion formula $$I^{k+1}(x) = I^k(x) + \Delta I(x; p^{i(k)}, I^k(x)), \quad (1)$$

wherein $I^k(x)$ approximates the unknown function I(x). In many algorithms (including ART), $\Delta I$ depends only on the projection of $I^k(x)$ taken from the same direction as $p^{i(k)}$.

When extending such an algorithm to the non-stationary situation of perfusion imaging as it was described above, a similar formula is needed for the iterative approximation of the parameter vector a(x) by a sequence $a^k(x)$.

Assume that the k-th element $a^k(x)$ of this sequence is already known and define $I^k(x,t) := I^*(a^k(x), t)$. The next iteration step for finding $a^{k+1}(x)$ must be carried out for one of the time points $t^i_j$ for which a projection $p^i_j$ is available. For this fixed time point $t^i_j$, the recursion formula (1) may analogously be applied, which yields $$I^{k+1}(x, t^i_j) = I^k(x, t^i_j) + \Delta I(x; p^i_j, I^k(x, t^i_j))$$
$$= I^*(a^k(x), t^i_j) + \Delta I(x; p^i_j, I^*(a^k(x), t^i_j))$$
$$= I^*(a^k(x), t^i_j) + \Delta I^{k,i}_j$$

From this equation the difference between the model function $I^*(a^{k+1}(x), t^i_j)$ at the new (unknown) parameter vector $a^{k+1}(x)$ and the (known) updated function $I^{k+1}(x, t^i_j)$ can be calculated as:

$$\chi^i_j = I^*(a^{k+1}(x), t^i_j) - I^{k+1}(x, t^i_j)$$
$$= I^*(a^{k+1}(x), t^i_j) - I^*(a^k(x), t^i_j) - \Delta I^{k,i}_j$$

A reasonable postulation is now to make $|\chi^i_j|$ as small as possible by an appropriate choice for $a^{k+1}(x)$. As the vector a has N components, this postulation alone would however have many solutions and thus convergence cannot be guaranteed. Therefore, it is better to adapt several (preferably all) components of $a^{k+1}(x)$ simultaneously by requiring the minimisation of $$\chi^2(x) = \sum_{i \in A, j \in B} (\chi_j^i)^2 \qquad (2)$$
$$= \sum_{i \in A, j \in B} (I^*(a^{k+1}(x), t_j^i) - I^*(a^k(x), t_j^i) - \Delta I_j^{k,i}(x))^2,$$

wherein A, B are index sets that may in principle be chosen arbitrarily for each iteration step, and wherein the number (|A|+|B|) of the terms is preferably greater or equal to N.

In order to guarantee a stable convergence (due to a balanced contribution of all components of a to the minimization), it is preferred to choose for the iteration step k→(k+1) only projections taken from the same direction $d^i$. This means that |A|=1 and |B|≧N in equation (2). Especially the function $$\chi^2(x) = \sum_{j=1}^{N} (\chi_j^i)^2 = \sum_{j=1}^{N} (I^*(a^{k+1}(x), t_j^i) - I^*(a^k(x), t_j^i) - \Delta I_j^{k,i}(x))^2$$

may be minimized in order to find for each voxel x the new parameter vector $a^{k+1}(x)$. This solution may be found, for instance, by a least-squares method or some other suitable procedure known from numerical mathematics.

In summary, each iteration step of the reconstruction algorithm can be realized by
  Computation of N estimates $I^*(a^k(x),t_j^i)$ for the time points $t_1^i, \ldots, t_N^i$ based on the already known parameter vector $a^k(x)$ and an (arbitrarily chosen) index i.
  Computation of N updates $\Delta I^{k,i}_1, \ldots, \Delta I^{k,i}_N$ using the acquired projections $p_j^i$ and said N estimates.
  Computing during backprojection for each voxel x the updated parameters $a^{k+1}(x)$ by minimizing $\chi^2(x)$.

As variants, the algorithm can also be carried out if the projection directions $d^i$ of the N projections $p_1^i, \ldots, p_N^i$ differ slightly. In particular, the projections acquired with an angular difference about 180° at the turning point of the C-arm movement can be considered simultaneously within a reconstruction iteration to improve stability. Furthermore, an anatomical reference data set can be used to reduce the number N of parameters $a_1(x), \ldots, a_N(x)$ by 1.

According to another approach, the parameter vector a(x) may be found by minimisation of an objective function like $$\chi^2 = \sum_{i,j} (p_j^i - P_i I^*(a(x), t_j^i))^2,$$

wherein 1≦i≦M, 1≦j≦N, and wherein $P_i$ denotes the operator projecting the image $I^*(a(x),t)$ according to the projection geometry $d^i$. In this case it is not necessary (or helpful) that all projections $p_j^i$ with the same superscript i belong to the same projection direction. In contrast to the diagram of FIG. 1, the $p_j^i$ may therefore be quite arbitrarily distributed over projection angles and time.

Minimisation of the function $\chi^2$ may e.g. be achieved by an iterative procedure. In this case it is preferred to use a (2D or 3D) sectional image of the region of interest as a starting value for $I^*(a(x),t_j^i)$. Such a "starting image" may be produced by any appropriate method, e.g. by backprojection from a set of projections. Moreover, the starting image may be taken from previously (e.g. days before the perfusion imaging) recorded data, thus minimising the X-ray exposure of the patient. Preferably, however, the starting image is produced immediately before the projections $p_j^i$ in order to correspond to the situation on these projections as close as possible.

The invention enables perfusion imaging on C-arm based X-ray systems as it does not require acquisition of (multiple) cross-sectional images with a frame rate in the order of 1 second. When applied on multi-slice CT (MSCT) systems, the invention facilitates perfusion protocols with considerably reduced dose.

Finally it is pointed out that in the present application the term "comprising" does not exclude other elements or steps, that "a" or "an" does not exclude a plurality, and that a single processor or other unit may fulfill the functions of several means. Moreover, reference signs in the claims shall not be construed as limiting their scope.

The invention claimed is:

1. An image processing apparatus for the reconstruction of time-dependent representations I(x,t) of an object, comprising:
  an approximation module with memory storing the N-dimensional parameter vector a(x) of a predetermined parametric model function $I^*(a(x),t)$ that approximates the function I(x,t);
  an input module for the reception of a set of projections $p_j^i$ of the object generated at times $t_j^i$, and
  an estimation module that is adapted to estimate the parameter vector a(x) with the help of said projections $p_j^i$.

2. The apparatus according to claim 1, further comprising an evaluation module for the determination of a perfusion map from the representation $I^*(a(x),t)$ of a vessel system.

3. The apparatus according to claim 1, wherein the representation I(x,t) and its approximation $I^*(a(x),t)$ describe, for each time t, a cross-sectional image of the object.

4. The apparatus according to claim 3, wherein the estimation of the parameter vector a(x) is based on an update function $\Delta I(x, p^{i(k)}, I^k(x))$ of an iterative algorithm for the reconstruction of a stationary cross-sectional image I(x), wherein $p^{i(k)}$ is a projection used in the k-th iteration step and $I^k(x)$ is the k-th estimate for I(x).

5. The apparatus according to claim 4, wherein the parameter vector a(x) is iteratively approximated by a sequence $a^k(x)$, and wherein the (k+1)-th iteration comprises the following steps:
  a) computation of estimates $I^*(a^k(x),t_j^i)$ for at least N of the times $t_j^i$, wherein I∈A and j∈B for some index sets A, B;
  b) computation of corresponding updates $\Delta I^{k,i}_j = \Delta I(x, p_j^i, I^*(a^k(x),t_j^i))$ with the help of said estimates $I^*(a^k(x),t_j^i)$ and the measured projections $p_j^i$ that correspond to the times $t_j^i$; and
  c) calculation of the new estimate $a^{k+1}(x)$ for the parameter vector a(x) by minimising $$\chi^2(x) = \sum_{i \in A, j \in B} (I^*(a^{k+1}(x), t_j^i) - I^*(a^k(x), t_j^i) - \Delta I_j^{k,i}(x))^2.$$

6. The apparatus according to claim 1, wherein a set of measured projections $p_j^i$ can be divided into M subsets, and wherein each subset comprises only projections $p_j^i$, j=1,...Q taken from the same or approximately the same direction ($d^i$) at different times $t_j^i$, and wherein Q≧N.

7. The apparatus according to claim 1, wherein the estimation of the parameter vector a(x) is based on the minimization of an objective function evaluating the deviation between measured projections $p^i_j$ and corresponding projections $P_i I^*(a^k(x), t^i_j)$ calculated from the model function, and wherein the objective function preferably is defined as $$\chi^2 = \sum_{i,j} (p^i_j - P_i I^*(a(x), t^i_j))^2.$$

8. The apparatus according to claim 1, wherein the estimation of the parameter vector a(x) makes use of an anatomical reference data set.

9. An X-ray examination system, comprising:
   a rotational X-ray apparatus for generating X-ray projections $p^i_j$ of an object from different directions;
   an image processing apparatus coupled to the X-ray apparatus and adapted to estimate based on said projections $p^i_j$ the N-dimensional parameter vector a(x) of a predetermined parametric model function I*(a(x),t) that approximates the representation I(x,t) of the object.

10. The system according to claim 9, wherein the image processing apparatus for the reconstruction of time-dependent representations I(x,t) of the object comprises:
    an approximation module with memory storing the N-dimensional parameter vector a(x) of the predetermined parametric model function I*(a(x),t) that approximates the function I(x,t);
    an input module for the reception of a set of projections $p^i_j$ of the object generated at times $t^i_j$, and
    an estimation module that is adapted to estimate the parameter vector a(x) with the help of said projections $p^i_j$.

11. The system according to claim 9, wherein the rotational X-ray apparatus is a C-arm system or a multi-slice CT system.

12. The system according to claim 9, further comprising an injection system for injecting a contrast agent into the blood flow of a patient.

13. A method for the reconstruction of time-dependent representations of an object, comprising the following steps:
    approximation of the function I(x,t) which describes the representations by a predetermined parametric model function I*(a(x),t); and
    estimation of the N-dimensional parameter vector a(x) with the help of a set of projections $p^i_j$ of the object generated at times $t^i_j$.

14. The method according to claim 13, wherein the projections $p^i_j$ are generated with a C-arm system or a multi-slice CT system.

15. A non-transitory computer readable medium encoded with a computer program for enabling carrying out a method according to claim 14.

16. A non-transitory record carrier on which a computer program according to claim 15 is stored.

17. An X-ray system suitable for determining a 3D dynamic process in an object, the system comprising:
    an x-ray source and an x-ray detector placed at opposite positions with respect to an examination space and simultaneously rotatable around said examination space for generating a plurality of x-ray projections; and
    a data processing unit for deriving from said plurality of x-ray projections a map of a time dependent 3D dynamic process in the object,
    wherein the 3D dynamic process is approximated by a predetermined model with a limited set of parameters, and
    wherein the data processing unit is arranged to estimate parameters in said limited set of parameters out of data in the x-ray projections.

18. The X-ray system according to claim 17, wherein the predetermined model approximates the perfusion of contrast medium in tissue.

19. The X-ray system according to claim 17, wherein the x-ray system is a C-arm x-ray device or a multi-slice CT system.

* * * * *